United States Patent [19]

Iizumi et al.

[11] Patent Number: 5,306,636

[45] Date of Patent: Apr. 26, 1994

[54] GENE, VECTOR AND TRANSFORMANT FOR THERMOSTABLE LIPASE AND PREPARATION OF THEM AND THERMOSTABLE LIPASE

[75] Inventors: Taro Iizumi, Isehara; Koichi Nakamura, Sagamihara; Tetsuro Fukase, Kamakura, all of Japan

[73] Assignee: Kurita Water Industries Ltd., Tokyo, Japan

[21] Appl. No.: 639,330

[22] Filed: Jan. 10, 1991

[51] Int. Cl.$^5$ .............. C12N 15/55; C12N 15/74; C12N 1/21; C12N 9/20

[52] U.S. Cl. ............... 435/252.3; 435/198; 435/69.1; 435/71.1; 435/71.2; 435/172.3; 435/252.33; 435/252.34; 435/320.1; 536/23.2; 935/6; 935/9; 935/11; 935/14; 935/27; 935/29; 935/56; 935/72

[58] Field of Search .......... 435/69.1, 71.1, 71.2, 435/172.1, 172.3, 198, 252.3, 252.33, 252.34, 320.1; 935/6, 9, 11, 14, 27, 29, 56, 72; 536/23.2

[56] References Cited

FOREIGN PATENT DOCUMENTS 0204284 12/1986 European Pat. Off. ....... C12N 9/20
0331376 9/1989 European Pat. Off. ..... C12N 15/00
2-190188 7/1990 Japan ........................ C12N 15/55
2216528 10/1989 United Kingdom ........ C12N 15/00

OTHER PUBLICATIONS

Kurta Water Co. "Pseudomonas KWI-56 strain-used for the Production . . . " Dewent Biotechnology Abstracts vol. 8(17)113–114 Abstract No. 89-10503.
Kugimiya et al. "Molecular Cloning and Nucleotide Sequence of the Lipase . . . " Biochem. Biophys. Res. Commun. vol. 141(1) 185–190.

*Primary Examiner*—Robert A. Wax
*Assistant Examiner*—Rebecca Prouty
*Attorney, Agent, or Firm*—Flynn, Thiel, Boutell & Tanis

[57] ABSTRACT

A thermostable lipase gene coding for a thermostable lipase, a vector having this gene, a transformant containing this vector, methods for preparing them and for preparing a thermostable lipase by cultivating the transformant are disclosed. The thermostable lipase gene is obtained from a cell belonging to the bacterial strain Pseudomonas sp. KWI-56 by a technique of genetic engineering. The thermostable lipase gene is inserted into a high expression vector, which is introduced into a cell of a host microorganism to prepare a transformant. By cultivating this transformant, a thermostable lipase can be produced.

3 Claims, 1 Drawing Sheet

Fig. 1

GENE, VECTOR AND TRANSFORMANT FOR THERMOSTABLE LIPASE AND PREPARATION OF THEM AND THERMOSTABLE LIPASE

FIELD OF THE INVENTION

The present invention relates to a gene, a vector and a transformant having a novel DNA-sequence for coding a thermostable lipase and to a process for preparing such a lipase. More particularly, it relates to a gene, a vector and a transformant having a novel DNA-sequence which codes for a thermostable lipase and which is produced using chromosomal DNA derived from a cell of the bacterial strain Pseudomonas sp. KWI-56, i.e., a bacterium producing a thermostable lipase; and to a process for preparing the thermostable lipase.

BACKGROUND OF THE INVENTION

A lipase is an enzyme that catalyzes the hydrolysis of triglycerides into free fatty acids and glycerol.

For utilizing lipases in an industrial scale, however, the reaction must be conducted at such a high temperature that the triglycerides to be treated are in a molten state, since most fatty oils composed of long chain saturated fatty acids are usually present as solids at ordinary temperatures. In addition, a long retention time within the enzyme reactor at a high temperature is required for carrying out a continuous enzyme reaction by employing an immobilized enzyme, so that the enzyme to be employed in such a reaction system should have a high thermostability.

As to the screening for finding thermostable lipases, it has been reported that, in particular, bacteria in the genus Pseudomonas can produce such thermostable lipases, for example, *Pseudomonas mephitica var. lipolytica* (Japanese Patent Publication No. 25553/1975), *Pseudomonas fragi* (Japanese Patent Application Kokai No. 280274/1986) and *Pseudomonas fluorescens* biotype I (Japanese Patent Application Kokai No. 58885/1982).

On the other hand, in recent years, genetic engineering techniques have been applied in the mass production of enzymes. Thus, a gene coding the objective enzyme is subjected to cloning and the resulting cloned DNA is ligated to yield an adequate high expression vector. The vector containing the gene of the objective enzyme is then introduced into a host cell of, such as, the bacterial strain *Escherichia coli* to effect a transformation. The resulting transformant is cultivated under optimum conditions for the production of the enzyme, whereby the objective enzyme can be easily produced in large amounts. Utilization of techniques of genetic engineering were attempted also in the production of lipases, wherein cloning of many lipase genes from various microorganisms had been carried out. There have been reported bacteria therefor of, for example, the genuses Staphylococcus, Pseudomonas, Bacillus and Geotrichum. Europ. Pat. Application No. 331376 A2 discloses a process for preparing a lipase by cloning the lipase gene from a bacterium of the genus Pseudomonas and utilizing this lipase gene. No mention is given, however, in this Patent Application as to a thermostable lipase.

As far as the inventors know, there is only a single report for *Bacillus stearothermophilus* concerning the cloning of thermostable lipase gene (Japanese Patent Application Kokai No. 228279/1987). There has not been known, in particular, any report for the cloning of a thermostable lipase gene derived from a microorganism of the genus Pseudomonas and for a process for preparing this lipase by a recombinant bacterium containing cloned thermostable lipase gene.

SUMMARY OF THE INVENTION

An object of the present invention is to provide a novel thermostable lipase gene and a method for expressing it.

Another object of the present invention is to provide a vector having such a thermostable lipase gene and a method for preparing it.

Still another object of the present invention is to provide a transformant having a recombinant DNA transformed with the above vector and a method for preparing it.

A further object of the present invention is to provide a process for preparing a thermostable lipase through the use of the above transformant.

The thermostable lipase gene according to the present invention has a nucleotide sequence represented by SEQ ID NO:1 and codes a thermostable lipase.

The vector according to the present invention has DNA containing the above mentioned thermostable lipase gene.

The method for the preparation of the thermostable lipase gene comprises cloning the gene which codes the thermostable lipase from the cell of a bacterium of Pseudomonas sp. KWI-56 (FERM BP-3178).

The method for preparing the vector according to the present invention comprises ligating the heat stable lipase gene to give a high expression vector.

The transformant according to the present invention comprises the cell of a host microorganism which has been transformed with the above vector.

The process for preparing the thermostable lipase according to the present invention comprises cultivating the above transformant and isolating the resulting thermostable lipase.

DETAILED DESCRIPTION OF THE INVENTION

The nucleotide sequence of the gene coding a thermostable lipase has been determined by the inventors by cloning this gene from the cell of a thermostable lipase-producing bacterium of the strain Pseudomonas sp. KWI-56, which sequence is represented by SEQ ID NO:1.

The Bacterial Strain Pseudomonas sp. KWI-56

The bacterial strain Pseudomonas sp. KWI-56 has been disclosed in Japanese Pat. Appl. Kokai No. 112979/1989 and has been deposited at the Japanese Fermentation Research Institute of Agency of Industrial Science and Technology, Japan with a deposition No. FERM BP-3178. It produces a lipase having a very high thermostability and an optimum reaction temperature in the range of 60°–65° C.

Below, the bacteriological properties of the bacterial strain Pseudomonas sp. KWI-56 are given. For evaluation of the bacteriological properties, the method and the culture medium described in "Classification and Identification of Microorganisms" of T. Hasegawa, published from Gakkai Shuppan Center; "Guide for the Identification of Medical Bacteria" of S. T. Cowan (Japanese Translation by R. Sakazaki, published from Kindai Shuppan) and "Lecture for new Bacterial Culture Media" of R. Sakazaki, published from Kindai Shuppan were employed. In the data given below, % values are on a weight basis.

a) Morphology
1) Size and Shape of the Cell:
   Rod, with a length of 2.2-3.0 μm and a width of 0.5-0.7 μm
2) Bimorphism of the Cell:
   Isolate or short chain
3) Motility:
   Recognized, having a single polar flagellum
4) Spore:
   Not formed
5) Gram stain:
   Negative
6) Acid-fastness:
   Negative b) Growth State
1) Nutrient broth agar plate culture:
   Circular, convex, with smooth and glossy surface, slightly yellowish white
2) Nutrient broth agar slant culture:
   Filament, ordinary growth, smooth and glossy surface, no formation of pigment, slightly yellowish white
3) Nutrient broth liquid culture:
   Ordinary growth, turbid, no formation of pigment
4) Nutrient broth gelatine stab culture:
   Ordinary growth, liquefied
5) Litmus milk:
   Slightly alkaline, liquefied c) Physiological Properties
1) Reduction of nitrates:
   Positive
2) Denitrification:
   Negative
3) MR test:
   Negative
4) VP test:
   Negative
5) Formation of indole:
   Negative
6) Formation of hydrogen sulfide:
   Slightly positive
7) Hydrolysis of starch:
   Negative
8) Utilization of citric acid:
   Positive in Koser medium, positive in Christensen medium
9) Utilization of inorganic nitrogen sources:
   Does not utilize sodium nitrate, but utilizes ammonium sulfate
10) Formation of pigment:
    No formation of pigment in Pseudomonas F agar, in Pseudomonas P agar (from the firm Difco Laboratories), in Kligler's culture medium (without indicator) and in TSI agar culture medium (without indicator)
11) Urease:
    Positive
12) Oxidase:
    Positive
13) Catalase:
    Positive
14) Growth range:
    Growing within a pH range of 4.5-8.5, with optimum pH: 5.5-7.0; growing within a temperature range of 15°-37° C., no growth at temperatures of 10° C. and 40° C., optimum temperature: at around 33° C.
15) Behavior to oxygen:
    Aerobic
16) O-F test:
    Oxidative
17) Formation of acid and gas from sugars according to Hugh-Leifson:
    Producing acid but no emission of gas from: L-arabinose, D-xylose, D-glucose, D-mannose, D-fructose, D-galactose, maltose, sucrose, lactose, trehalose, D-sorbitol, D-mannitol, inositol and glycerol;
    No formation of sugar or gas from starch
18) Accumulation of poly-$\beta$-hydroxybutyric acid:
    Positive
19) Cleavage of protocatechuic acid:
    Ortho-type
20) Oxidation of gluconic acid
    Positive
21) Decarboxylation of alginine:
    Negative
22) Decarboxylation of lysine:
    Positive
23) Production of lipase:
    Positive
24) Utilization of carbonic compounds according to the method of Stanier et al:
    Capable of growing with:
      glucose, galactose, lactose, arabinose, maltose, sorbitol, L-threonine, L-alginine, L-alanine, D-alanine, acetamide, DL-$\beta$-hydroxybutyric acid;
    No growth with:
      glycine, inulin, itaconic acid and mesaconic acid Physicochemical Properties of the Thermostable Lipase The thermostable lipase prepared from the cells of the bacterial strain Pseudomonas sp. KWI-56 has the following physicochemical properties:

1) Function:
   It decomposes palm oil, olive oil, coconut oil and beef tallow to a degree of 95% or higher at a reaction temperature of 50° C. during 20 hours.
2) Substrate specificity:
   It decomposes triglycerides in a facilitated manner, in particular, trimyristin, tricaprin and tricaprylin. It decomposes spermaceti, but not lower alcohol esters of oleic acids.
3) Optimum acting pH and stable pH range:
   With olive oil as the substrate, the optimum acting pH exists at 5.5-7.0, with a stable pH range of 4-10.
4) Range of adaptable acting temperature:
   With olive oil as the substrate, 60°-65° C.
5) Thermal stability:
   Stable for 24 hours at pH 7.0 up to a temperature of 60° C.
6) Molecular weight:
   33,000 determined by an SDS (sodium dodecyl sulfate)—polyacrylamide gel electrophoresis.
7) Condition of deactivation in pH, temperature etc.:
   At pH ranges below 3 and not lower than 12, it is subject to deactivation after 24 hours at 37° C. At pH 7.0, it is subject to deactivation to an extent of 82% after 24 hours at 70° C.

8) Inhibition:

Among metal ions, $Cu^{2+}$, $Zn^{2+}$, $Hg^{2+}$ and $Sn^{2+}$ cause deactivation of this enzyme. Addition of $Ca^{2+}$ does not affect the enzyme activity. It is inhibited to an extent of 50–80% by a bile salt, such as, sodium cholate, sodium deoxycholate, sodium taurocholate and so on, in a reaction mixture containing 0.5% of a surfactant and to an extent of over 90% with other surfactants.

9) Method of purification:

Cells of the bacterial strain Pseudomonas sp. KWI-56 were cultivated in a culture medium containing 1% of oleic acid, 2% of polypeptone, 0.1% of $KH_2PO_4$, 0.05% of $MgSO_4.7H_2O$ and 0.1% of yeast extract. To this culture broth, acetone was added in an amount of 50% and the mixture was centrifuged in order to remove the cell residues. The supernatant was concentrated by ultrafiltration and was purified by repeated acetone-precipitation by making use of the favorable property of this enzyme of withstanding acetone treatment. Finally, gel filtration was performed, whereby a purified and electrophoretically identical product of the enzyme was obtained. The specific activity thereof was determined to be 2550 IU/mg protein.

10) Isoelectric point pI:

From the measurement by an isoelectric point electrophoresis, pI=5.0 was determined.

11) Sugar content:

No coloration on a phenol-sulfuric acid method was observed and, thus, no sugar content was recognized.

12) Elementary analysis:

H=6.8%, C=47.5%, N=14.7%

Cloning of the Lipase Gene

The thermostable lipase gene according to the present invention is obtained by a technique of genetic engineering from Pseudomonas sp. KWI-56. The cloning was effected in the following manner:

The chromosomal DNA containing the thermostable lipase gene was isolated from Pseudomonas sp. KWI-56 in accordance with ordinary procedures. For this, techniques can be employed such as the method proposed by Marmur [Marmur, J.: "J. Mol. Biol.", 3, 208 (1961)] and the method proposed by Smith et al [Smith, M., G.,: "Method in Enzymology", Academic Press, New York, 12, part A, p 545 (1967)].

The thus isolated chromosomal DNA, on the one hand, and a selected vector DNA, on the other hand, were digested using a restriction enzyme. The DNA fragments of them were mixed and treated by a DNA ligase, whereby the ligation of the chromosomal DNA with the vector DNA was effected.

As the restriction enzyme, there may be employed, for example, BamHI, EcoRI, PstI, SalI, Sau3AI and so on. For the DNA vector, there may be employed, for example, known plasmid vectors, such as, pUC18, pUC19, pBR322 and so on and known phage vectors, such as, M13mp18, λgt10 and so on.

With the thus obtained recombinant vector, a cell of a host microorganism, such as, *Escherichia coli, Bacillus subtilis,* yeast and so on is transformed to thereby obtain a transformant. For transformation, known methods such as the calcium chloride method and so on may be employed. From the thus obtained transformants resulting from the above procedure, the bacteria cells having a DNA containing the lipase gene can be isolated by screening. This can be effected by, for example, the method proposed by Kugimiya et al [Kugimiya, S.: "Biochem. Biophys. Res. Commun.", 141, 185 (1986)], by isolating the cells of the bacterial strain forming a clear zone incidental to the hydrolysis of tributyrin on a tributyrin-agar culture medium.

Other cell strains of *Escherichia coli, Bacillus subtilis,* yeast and so on, without the lipase gene, do not form a clear zone on the culture medium, whereas the bacterial strains transformed with the thermostable lipase gene will form a clear zone around the colony.

The so obtained transformant is then subjected to a known treatment, such as the alkali-SDS method to isolate the recombinant vector. The isolated recombinant vector is then treated by a restriction enzyme to obtain the foreign DNA fragment containing thermostable lipase gene.

After purification, the DNA fragment containing the thermostable lipase gene can be obtained The DNA fragment containing the thermostable lipase gene can be confirmed in a manner such that the above recombinant vector is subjected to subcloning using various restriction enzymes and the resulting recombinant vector is introduced into the cell of a host organism and each of the thus obtained transformants is cultivated on a tributyrin agar medium in order to detect the occurrence of a clear zone around the colony.

The nucleotide sequence of the thermostable lipase gene obtained as above was determined to be that of SEQ ID NO:1.

Nucleotide sequences can be determined by a known method, for example, in accordance with the "dideoxy method" [Sanger F.: "Proc. Natl. Acad. Sci. U.S.A.", 74 5463 (1977)].

Proof of the Lipase Gene Cloned as Above to be the Gene that Produces a Thermostable Lipase Whether the thermostable lipase produced by the bacterial strain Pseudomonas sp. KWI-56 is derived from the gene obtained as above or not, can be confirmed by detecting the existence or concordance of the primary structure of the lipase protein with the amino acid sequence corresponding to the nucleotide sequence of the lipase gene.

The amino acid composition of the thermostable lipase is obtained after purification from the supernatant of culture medium of the bacterial strain Pseudomonas sp. KWI-56 by hydrolyzing the lipase and analyzing using an amino acid analyzer. The partial amino acid sequence can be determined by means of a liquid phase Edman degradation, from the N-terminal amino acid or by the so-called carboxypeptidase method from the C-terminal amino acid.

Vector and Transformant

The vector according to the present invention which has the thermostable lipase gene is obtained from insertion of the above-mentioned thermostable lipase gene into an expression vector, such as a plasmid vector, phase vector or so on. The vector containing the thermostable lipase gene can be introduced into the cell of a host microorganism, such as, *Escherichia coli* or so on, whereby the transformant for the production of thermostable lipase according to the present invention can be obtained.

Preparation of Thermostable Lipase by Recombinant Transformant

According to the present invention, the thermostable lipase gene isolated as described above can be utilized to produce the thermostable lipase. Here, the thermostable lipase gene is inserted into an adequate vector and the modified vector is introduced into the cell of a host microorganism to produce a recombinant transformant. As the host microorganism, bacteria of, for example, *Escherichia coli, Pseudomonas* and *Bacillus subtilis* may be employed. For the vector, those which are stable in the cell of the microorganism selected as the host and capable of autonomous replication and permissible of expression of the recombinant gene can be employed, for example, pUC18, pHSG299, pBP322, M13mp18 and λgt10 for the host microorganism of *Escherichia coli*, pKT240, pSUP104 and pVK101 for the host microorganism of Pseudomonas, and pUB110, pHY300PLK and so on for the host microorganism of *Bacillus subtilis*. For effecting the introduction of the so treated plasmid into the cell of the host organism, known practices, such as, calcium treatment, electroporation, conjugal transfer and so on can be employed.

The thus obtained transformant containing the plasmid vector having the thermostable lipase gene is cultivated under optimum conditions for producing the lipase. From the culture supernatant or from the cell lysate, the objective lipase can be collected.

As explained above, an industrial production of the thermostable lipase can be easily attained by making use of the transformant having DNA containing therein the segment of the thermostable lipase gene identified by the inventors. By a site-directed mutagenesis on the lipase gene, a novel material for producing a lipase possessed of a new capability of alkali-resistance, surfactant-resistance and so on may be realized.

PREFERRED EMBODIMENT OF THE INVENTION

Below, the present invention will be described concretely by way of Examples, wherein it should be noted that the present invention should never be restricted by these Examples. The % values given are on the weight basis.

EXAMPLE 1

(1) Preparation of Chromosomal DNA Library of the Bacterial Strain Pseudomonas sp. KWI-56

A small aliquot of living cells of the bacterial strain Pseudomonas sp. KWI-56 was inoculated in 200 ml of an NB medium (1% of nutrient broth, 1% of peptone, 0.5% of NaCl, pH=7.0) and was cultivated at 30° C. for 24 hours under shaking. Thereafter, bacteria cells were collected and washed and then suspended in 12 ml of 0.1M trishydrochloride buffer with 10 mM EDTA of pH 8.0. 1 mg of lysozyme was added thereto and the mixture was allowed to stand at 37° C. for 10 minutes. To this mixture was added 600 μl of 10% SDS and the mixture was allowed to stand at 37° C. for 30 minutes to effect bacteriolysis. After the further addition of 600 μl of 3M NaCl, the mixture was subjected to extraction with phenol 3 times, whereupon the phenol extract was washed with ether and then subjected to ethanol-precipitation. The resulting precipitate was dried and then dissolved in 10 ml of SSC solution and, after the addition thereto of 0.5 mg of ribonuclease A, the mixture was allowed to stand at 37° C. for 30 minutes. The mixture was then subjected again to phenol treatment three times and, after washing with ether, the DNA was collected by precipitation by ethanol. The precipitate was dried and then dissolved in a SSC solution. 3.5 mg of chromosomal DNA were obtained. The resulting chromosomal DNA was then subjected to partial digestion by a restriction enzyme, Sau3AI, under such a condition that the chain length of the resulting DNA fragments would be in the range from 4 to 10 kb. As the DNA vector, plasmid: pUC19 was employed. pUC19 was subjected to digestion by the restriction enzyme BamHI and the resulting fragments were treated with alkali phosphatase.

The partial digestion product of the chromosomal DNA of the bacterial strain Pseudomonas sp. KWI-56 and the digestion product of plasmid pUC19 were mixed at a mixing ratio of 2:1, whereupon ligation was effected using the DNA-Ligation Kit of Takara Shuzo Co., Ltd. at 16° C. for 30 minutes. From the bacterial strain *Escherichia coli* HB101, a transformant was prepared by the method of Hanahan [Hanahan, D.: "Gene", 10 63 (1980)] with the above obtained recombinant plasmid by the calcium treatment.

(2) Isolation of Plasmid Joined with the Thermostable Lipase Gene

The transformant obtained as above was cultivated on an LB agar containing ampicillin in an amount of 50 μg/ml and 1% of tributyrin. After cultivation at 37° C. for 48 hours, 14 bacteria strains, each exhibiting a clear zone around the cultivation colony, were obtained from among about 16,400 transformants.

Each of 14 clear zone-forming strains was cultivated at 37° C. for 24 hours in 5 ml of an LB liquid culture medium, each containing 50 μg/ml of ampicillin, under shaking. The culture broth was subjected to ultrasonic treatment for disintegrating the bacteria cells, whereupon the lipase activity was detected for each of the culture broths. For the detection, a rotary agitation method was employed. Thus, 5 ml of 1/20M phosphate buffer (pH 7.0), 1 ml of olive oil and 1 ml of enzyme solution were charged in a reactor and the mixture was caused to react at 37° C. for 60 minutes at a stirrer rotation rate of 500 rpm. The reaction was caused to cease by adding 20 ml of ethanol, whereupon the amount of the free fatty acid produced was titrated using 1/20N KOH solution. Here, for the evaluation of enzyme activity, such an amount of enzyme that liberates 1 μmol of the fatty acid per 1 minute was employed as 1 unit (1 U) of activity.

Among the 14 clear zone-forming strains, one strain exhibiting a lipase activity of 0.025 U/ml was isolated. This transformant was denoted as the strain "SA-3".

The strain SA-3 was cultivated in 5 ml of an LB liquid medium containing 50 μg of ampicillin per milliliter of the medium at 37° C. for 24 hours under shaking, whereupon the plasmid was extracted by means of an alkali-SDS method. This plasmid was found to have 11.5 kb of foreign DNA fragments. This plasmid was named as "pLP6".

(3) Analysis of pLP6

The plasmid pLP6 was subjected to subcloning by various restriction enzymes. The smallest DNA fragment capable of coding the thermostable lipase gene and the gene participating in the expression of the activity therefor was determined based on the criteria as to whether a clear zone formed around the colony in the culture of strain *Escherichia coli* HB101 containing the recombinant plasmid on a tributyrin-LB plate.

Figure 1:
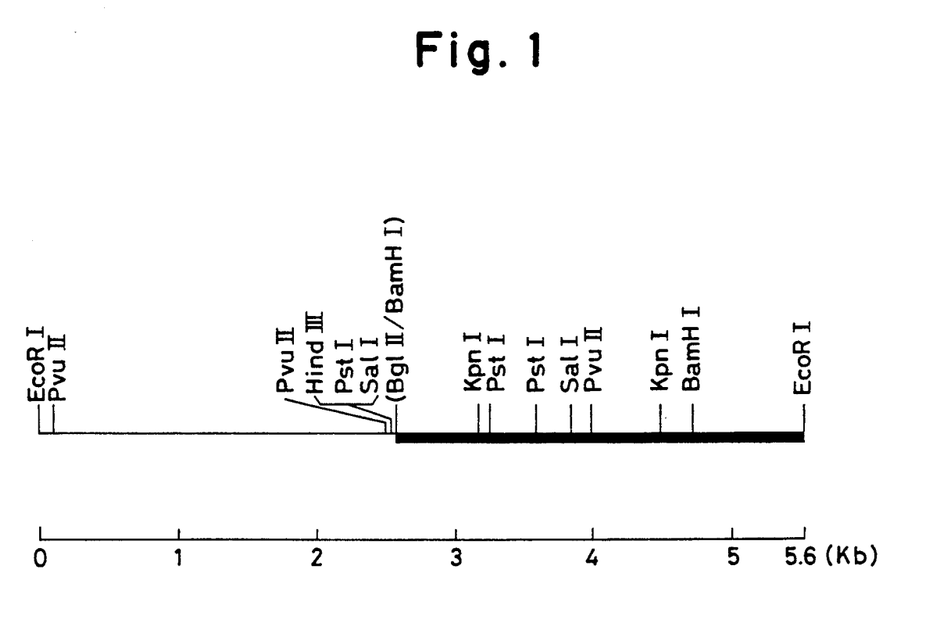
FIG. 1 is a restriction map of plasmid pLP64.

The results showed that a BgIII - EcoRI fragment of 2.9 kb was the smallest DNA fragment that coded for the thermostable lipase gene and the gene participating in the expression of the activity therefor. This fragment was ligated to plasmid pUC19 which was digested by BamHI and EcoRI. The recombinant plasmid was named as "pLP64". The restriction map of pLP64 digested by restriction enzymes is given in FIG. 1. In FIG. 1, the thin-lined portion represents the gene derived from plasmid pUC19 and the thick-lined portion represents the gene derived from the chromosomal DNA of the bacterial strain Pseudomonas sp. KWI-56.

(4) Determination of the Nucleotide Sequence of the Thermostable Lipase Gene

Before the determination of the base sequence, the 2.9 kb BglII - EcoRI fragment was subjected to subcloning with a phage vector of, for example, M13mp18 or mp19, to prepare various deletion phages using the Kilobase Deletion Kit of Takara Shuzo Co., Ltd. Using them as the template, the entire nucleotide sequence of the 2.9 kb BglII - EcoRI fragment was determined by means of the so-called dideoxy method. It was recognized from this determination that an open reading frame exists as given in SEQ ID NO:2. The amino acid sequence determined by the above nucleotide sequence was concurrently given in SEQ ID NO:2.

(5) Determination of the Amino Acid Composition of the Thermostable Lipase Gene and of the N-terminal and C-terminal Amino Acids Using 1 mg of the thermostable lipase obtained by purifying the supernatant of the cultivation broth of the bacterial strain Pseudomonas sp. KWI-56, the amino acid sequence thereof was successively determined from the N-terminal amino acid by the liquid phase Edman degradation method. The results showed that the amino acid sequence from the N-terminal of the lipase consists of alanine-asparagine-glycine. This sequence was found to be present at the position from 1st to 3rd sites of SEQ ID NO:2.

Then, 2 mg of the thermostable lipase were treated using about 36 μg of carboxypeptidase A and the amino acids successively liberated were determined, whereby liberation of a considerable amount of valine was recognized. From this result, it was judged that the C-terminal amino acid of the thermostable lipase is valine. The C-terminal amino acid determined by the nucleotide sequence was also found to be valine.

From these analyses, the thermostable lipase is composed of the amino acid sequence from the 1st to the 320th site, as given in SEQ ID NO:2. The amino acid sequence from the −44th site to the −1st site of SEQ ID NO:2 constitutes the signal peptide. The last triplet TAA of SEQ ID NO:2, i.e., the triplet from the 1093rd site to the 1095th site is the termination codon.

Thereafter, comparison between the amino acid composition of the thermostable lipase protein and that determined from the nucleotide sequence was carried out. 50 μg of the thermostable lipase were dissolved in 6N hydrochloric acid solution and treated at 110° C. for 24 hours, whereupon the hydrolyzed amino acids were determined.

The cystine residues were analyzed by the manner as above, after subjecting the thermostable lipase to oxidation with performic acid. The amount of tryptophan residues was calculated from the comparison of the amount of tyrosine residue from the absorbance data at 294.4 nm and at 280.0 nm of a 0.1 % aqueous solution of the thermostable lipase. The calculated amino acid composition of the lipase determined by the nucleotide sequence was obtained based on the amino acid composition in the segment of the DNA sequence from the 1st to the 320th amino acid of SEQ ID NO:2. It was found that a close coincidence existed between the analyzed amino acid composition with the calculated amino acid composition based on the determined nucleotide sequence, as shown in Table 1.

TABLE 1

| Amino Acid | Amino Acid Composition | |
|---|---|---|
| | Determed. for Thermostable Lipase | Calculated from Base Sequence |
| Asx | 32.1 | 32 |
| Thr | 30.1 | 32 |
| Ser | 21.1 | 24 |
| Glx | 21.8 | 21 |
| Pro | 11.6 | 11 |
| Gly | 35.7 | 36 |
| Ala | 39.9 | 39 |
| Cys | 0.4 | 2 |
| Val | 28.7 | 30 |
| Met | 0.9 | 1 |
| Ile | 9.9 | 11 |
| Leu | 34.0 | 33 |
| Tyr | 14.4 | 15 |
| Phe | 6.8 | 7 |
| His | 6.6 | 7 |
| Lys | 8.1 | 7 |
| Arg | 8.7 | 9 |
| Trp | 5.3 | 3 |
| Total | 316.1 | 320 |

From the above, it was found that the cloned lipase gene was that which gives the thermostable lipase derived from the bacterial strain Pseudomonas sp. KWI-56.

Since the N-terminal amino acid of the thermostable lipase was alanine at the 1st site of SEQ ID NO:2, the lipase will be matured by cleavage at the portion between proline at the −1st site and alanine at the 1st site after the translation.

In the plasmid pLP64, a further gene section participating in the expression of the activity of the thermostable lipase gene is coded downstream of this thermostable lipase gene.

(6) Production of the Thermostable Lipase by *Escherichia coli*

In a 500 ml Sakaguchi flask, 100 ml of an LB liquid medium added to 50 μg of ampicillin per milliliter of the medium were charged and, to this liquid medium, a preculture product of the bacterial strain *Escherichia coli* HB101 having plasmid pLP64 was inoculated in an amount of the inoculated cells of 1% and cultivated at 37° C. for 14 hours under shaking. The bacterium cells were collected, washed and then suspended in 100 ml of 20 mM trishydrochloride buffer (pH 7.5). The suspension was subjected to an ultrasonic treatment for disintegrating the bacteria cells, whereupon the suspension was centrifugated in order to remove the residues of the bacteria cells. The lipase activity of the supernatant from the centrifugation was determined by means of the rotary agitation method explained previously, whereby a lipase activity of 23.0 U/ml was detected. A residual lipase activity of this supernatant of the centrifugation after it had been heat treated at 60° C. for 1 hour revealed no deactivation.

We claim:

1. A thermostable lipase gene consisting essentially of a DNA obtained by cloning a chromosomal DNA from Pseudomonas sp. KWI-56, said obtained DNA encoding a thermostable lipase and having the nucleotide sequence of SEQ ID NO:1, said SEQ ID NO: 1 being:

```
GCC GAT GGC TAC GCG GCG ACG CGT TAT CCG ATC
                                       ATC CTC GTG   42

CAC GGG CTC TCG GGT ACC GAC AAG TAC GCC GGC
                                       GTG GTC GAG  84

TAT TGG TAT GGC ATC CAG GAA GAC CTG CAG CAG
                                       AAC GGT GCG 126

ACC GTC TAC GTC GCG AAC CTG TCG GGG TTC CAG
                                       AGC GAC GAC 168

GGC GCG AAC GGG CGC GGC GAA CAG TTG CTC
                                       GCT TAC GTG AAG 210

ACG GTG CTC GCG GCG ACG GGC GCG ACC AAG
                                       GTC AAT CTC GTC 252

GGC CAC AGC CAG GGC GGC CTC ACG TCG CGC TAT
                                       GTC GCG GCC 294

GTC GCG CCC GAT CTC GTG GCG TCG GTG ACG ACG
                                       ATC GGC ACG 336
```

CCG CAT CGC GGC TCC GAG TTT GCC GAC TTC GTG

CAG AAC GTG 378

CTG GCG TAC GAT CCG ACC GGG CTT TCG TCA TCG

GTG ATC GCC 420

GCG TTC GTC AAT GTG TTC GGC ATC CTG ACG AGC

AGC AGC CAC 462

AAC ACG AAC CAG GAC GCG CTC GCC GCG CTG CAG

ACG CTG ACC 504

ACC GCC CGG GCT GCC ACG TAC AAC CAG AAC TAT

CCG AGC GCG 546

GGC CTG GGT GCG CCG GGC AGT TGC CAG ACC

GGC GCG CCG ACC 588

GAA ACC GTC GGC GGC AAC ACG CAC CTG CTG TAT

TCG TGG GCC 630

GGC ACG GCG ATC CAG CCG ACG CTT TCG GTG TTC

GGC ATC ACG 672

GGC GCG ACC GAC ACG AGC ACC GTT CCG CTC GTT

GAT CTG GCG 714

AAC GTG CTC GAC CCG TCG ACG CTC GCG CTG TTC

GGC ACC GGC 756

ACG GTG ATG ATC AAC CGC GGC TCC GGG CAG AAC

GAC GGG CTC 798

GTG TCG AAG TGC AGT GCG CTG TAC GGC AAG GTG

CTG AGT ACG 840

AGC TAC AAG TGG AAC CAC CTC GAC GAG ATC AAC

CAG CTG CTC 882

GGC GTG CGC GGC GCG TAT GCG GAA GAT CCG

GTC GCG GTG ATC 924

CGC ACG CAT GCG AAC CGG CTG AAG CTG GCG

GGC GTG 960.

2. A vector consisting essentially of an expression vector having an inserted DNA containing a thermostable lipase gene having the nucleotide sequence of SEQ ID NO:1, said SEQ ID NO:1 being:

GCC GAT GGC TAC GCG GCG ACG CGT TAT CCG ATC

ATC CTC GTG 42

CAC GGG CTC TCG GGT ACC GAC AAG TAC GCC GGC

GTG GTC GAG 84

TAT TGG TAT GGC ATC CAG GAA GAC CTG CAG CAG

AAC GGT GCG 126

ACC GTC TAC GTC GCG AAC CTG TCG GGG TTC CAG

AGC GAC GAC 168

GGC GCG AAC GGG CGC GGC GAA CAG TTG CTC

GCT TAC GTG AAG 210

ACG GTG CTC GCG GCG ACG GGC GCG ACC AAG

GTC AAT CTC GTC 252

GGC CAC AGC CAG GGC GGC CTC ACG TCG CGC TAT

GTC GCG GCC 294

GTC GCG CCC GAT CTC GTG GCG TCG GTG ACG ACG

ATC GGC ACG 336

CCG CAT CGC GGC TCC GAG TTT GCC GAC TTC GTG

CAG AAC GTG 378

CTG GCG TAC GAT CCG ACC GGG CTT TCG TCA TCG

GTG ATC GCC 420

GCG TTC GTC AAT GTG TTC GGC ATC CTG ACG AGC

AGC AGC CAC 462

AAC ACG AAC CAG GAC GCG CTC GCC GCG CTG CAG

ACG CTG ACC 504

ACC GCC CGG GCT GCC ACG TAC AAC CAG AAC TAT

CCG AGC GCG 546

GGC CTG GGT GCG CCG GGC AGT TGC CAG ACC

GGC GCG CCG ACC 588

GAA ACC GTC GGC GGC AAC ACG CAC CTG CTG TAT

TCG TGG GCC 630

GGC ACG GCG ATC CAG CCG ACG CTT TCG GTG TTC

GGC ATC ACG 672

GGC GCG ACC GAC ACG AGC ACC GTT CCG CTC GTT

GAT CTG GCG 714

AAC GTG CTC GAC CCG TCG ACG CTC GCG CTG TTC

GGC ACC GGC 756

ACG GTG ATG ATC AAC CGC GGC TCC GGG CAG AAC

GAC GGG CTC 798

GTG TCG AAG TGC AGT GCG CTG TAC GGC AAG GTG

CTG AGT ACG 840

AGC TAC AAG TGG AAC CAC CTC GAC GAG ATC AAC

CAG CTG CTC 882

GGC GTG CGC GGC GCG TAT GCG GAA GAT CCG

GTC GCG GTG ATC 924

CGC ACG CAT GCG AAC CGG CTG AAG CTG GCG

GGC GTG 960.

3. A transformant consisting essentially of a bacterial cell having a recombinant DNA encoding a thermostable lipase and having the nucleotide sequence of SEQ ID NO:1, said SEQ ID NO:1 being:

```
GCC GAT GGC TAC GCG GCG ACG CGT TAT CCG ATC
                                ATC CTC GTG   42
CAC GGG CTC TCG GGT ACC GAC AAG TAC GCC GGC
                                GTG GTC GAG   84
TAT TGG TAT GGC ATC CAG GAA GAC CTG CAG CAG
                                AAC GGT GCG  126
ACC GTC TAC GTC GCG AAC CTG TCG GGG TTC CAG
                                AGC GAC GAC  168
GGC GCG AAC GGG CGC GGC GAA CAG TTG CTC
                                GCT TAC GTG AAG  210
ACG GTG CTC GCG GCG ACG GGC GCG ACC AAG
                                GTC AAT CTC GTC  252
GGC CAC AGC CAG GGC GGC CTC ACG TCG CGC TAT
                                GTC GCG GCC  294
GTC GCG CCC GAT CTC GTG GCG TCG GTG ACG ACG
                                ATC GGC ACG  336
CCG CAT CGC GGC TCC GAG TTT GCC GAC TTC GTG
                                CAG AAC GTG  378
CTG GCG TAC GAT CCG ACC GGG CTT TCG TCA TCG
                                GTG ATC GCC  420
GCG TTC GTC AAT GTG TTC GGC ATC CTG ACG AGC
                                AGC AGC CAC  462
AAC ACG AAC CAG GAC GCG CTC GCC GCG CTG CAG
                                ACG CTG ACC  504
ACC GCC CGG GCT GCC ACG TAC AAC CAG AAC TAT
                                CCG AGC GCG  546
GGC CTG GGT GCG CCG GGC AGT TGC CAG ACC
                                GGC GCG CCG ACC  588
GAA ACC GTC GGC GGC AAC ACG CAC CTG CTG TAT
                                TCG TGG GCC  630
GGC ACG GCG ATC CAG CCG ACG CTT TCG GTG TTC
                                GGC ATC ACG  672
GGC GCG ACC GAC ACG AGC ACC GTT CCG CTC GTT
                                GAT CTG GCG  714
AAC GTG CTC GAC CCG TCG ACG CTC GCG CTG TTC
                                GGC ACC GGC  756
ACG GTG ATG ATC AAC CGC GGC TCC GGG CAG AAC
                                GAC GGG CTC  798
GTG TCG AAG TGC AGT GCG CTG TAC GGC AAG GTG
                                CTG AGT ACG  840
AGC TAC AAG TGG AAC CAC CTC GAC GAG ATC AAC
                                CAG CTG CTC  882
GGC GTG CGC GGC GCG TAT GCG GAA GAT CCG
                                GTC GCG GTG ATC  924
CGC ACG CAT GCG AAC CGG CTG AAG CTG GCG
                                GGC GTG  960.
                * * * * *
```

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 960 base pairs
        ( B ) TYPE: nucleic acid
        ( C ) STRANDEDNESS: single
        ( D ) TOPOLOGY: linear     ( i i ) MOLECULE TYPE: Genomic DNA     ( i i i ) HYPOTHETICAL: yes     ( i v ) ANTI-SENSE: no     ( v i ) ORIGINAL SOURCE:
        ( A ) ORGANISM: Pseudomonas sp.
        ( C ) INDIVIDUAL ISOLATE: KWI-56
        ( G ) CELL TYPE: unicellular organism     ( v i i ) IMMEDIATE SOURCE:
        ( A ) LIBRARY: genomic
        ( B ) CLONE: SA-3

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( K ) RELEVANT RESIDUES IN SEQ ID NO: 1: FROM 1 TO 960

( x i ) SEQUENCE DESCRIPTION: SEQ ID NO: 1:

```
GCC GAT GGC TAC GCG GCG ACG CGT TAT CCG ATC ATC CTC GTG      42
CAC GGG CTC TCG GGT ACC GAC AAG TAC GCC GGC GTG GTC GAG      84
TAT TGG TAT GGC ATC CAG GAA GAC CTG CAG CAG AAC GGT GCG     126
ACC GTC TAC GTC GCG AAC CTG TCG GGG TTC CAG AGC GAC GAC     168
GGC GCG AAC GGG CGC GGC GAA CAG TTG CTC GCT TAC GTG AAG     210
ACG GTG CTC GCG GCG ACG GGC GCG ACC AAG GTC AAT CTC GTC     252
GGC CAC AGC CAG GGC GGC CTC ACG TCG CGC TAT GTC GCG GCC     294
GTC GCG CCC GAT CTC GTG GCG TCG GTG ACG ACG ATC GGC ACG     336
CCG CAT CGC GGC TCC GAG TTT GCC GAC TTC GTG CAG AAC GTG     378
CTG GCG TAC GAT CCG ACC GGG CTT TCG TCA TCG GTG ATC GCC     420
GCG TTC GTC AAT GTG TTC GGC ATC CTG AGC AGC AGC CAC         462
AAC ACG AAC CAG GAC GCG CTC GCC GCG CTG CAG ACG CTG ACC     504
ACC GCC CGG GCT GCC ACG TAC AAC CAG AAC TAT CCG AGC GCG     546
GGC CTG GGT GCG CCG GGC AGT TGC CAG ACC GGC GCG CCG ACC     588
GAA ACC GTC GGC GGC AAC ACG CAA CTG CTG TAT TCG TGG GCC     630
GGC ACG GCG ATC CAG CCG ACG CTT TCG GTG TTC GGC ATC ACG     672
GGC GCG ACC GAC ACG AGC ACC GTT CCG CTC GTT GAT CTG GCG     714
AAC GTG CTC GAC CCG TCG ACG CTC GCG CTG TTC GGC ACC GGC     756
ACG GTG ATG ATC AAC CGC GGC TCC GGG CAG AAC GAC GGG CTC     798
GTG TCG AAG TGC AGT GCG CTG TAC GGC AAG GTG CTG AGT ACG     840
AGC TAC AAG TGG AAC CAC CTC GAC GAG ATC AAC CAG CTG CTC     882
GGC GTG CGC GGC GCG TAT GCG GAA GAT CCG GTC GCG GTG ATC     924
CGC ACG CAT GCG AAC CGG CTG AAG CTG GCG GGC GTG             960
```

( 2 ) INFORMATION FOR SEQ ID NO: 2:

( i ) SEQUENCE CHARACTERISTICS:
        ( A ) LENGTH: 1095 base pairs and 364 amino acids
        ( B ) TYPE: nucleic acid and amino acid
        ( C ) STRANDEDNESS: single
        ( D ) TOPOLOGY: linear     ( i i ) MOLECULE TYPE: Genomic DNA and protein     ( i i i ) HYPOTHETICAL: yes     ( i v ) ANTI-SENSE: no (vi) ORIGINAL SOURCE:
  (A) ORGANISM: Pseudomonas sp.
  (C) INDIVIDUAL ISOLATE: KWI-56
  (G) CELL TYPE: unicellular organism (vii) IMMEDIATE SOURCE:
  (A) LIBRARY: genomic
  (B) CLONE: SA-3

(ix) FEATURE:
  (A) NAME/KEY: signal peptide
  (B) LOCATION: -44 to -1
  (C) IDENTIFICATION METHOD: Edman degradation Method
  (D) OTHER INFORMATION:

(ix) FEATURE:
  (A) NAME/KEY: mature protein
  (B) LOCATION: 1 to 320
  (C) IDENTIFICATION METHOD: Edman degradation Method
  (D) OTHER INFORMATION: expresses lipase (x) PUBLICATION INFORMATION:
  (A) AUTHORS:
  (B) TITLE:
  (C) JOURNAL:
  (D) VOLUME:
  (E) ISSUE:
  (F) PAGES:
  (G) DATE:
  (K) RELEVANT RESIDUES IN SEQ ID NO: 2: FROM 1 TO 1095

(xi) SEQUENCE DESCRIPTION: SEQ ID NO: 2:

```
ATG GCC AGA ACG ATG CGT TCC AGG GTG GTG GCA GGA GCA GTG    42
Met Ala Arg Thr Met Arg Ser Arg Val Val Ala Gly Ala Val
            -40                     -35

GCA TGC GCG ATG AGC ATC GCG CCG TTC GCG GGG ACG ACC GCA    84
Ala Cys Ala Met Ser Ile Ala Pro Phe Ala Gly Thr Thr Ala
-30             -25                     -20

GTG ATG ACG CTC GCG ACG ACG CAC GCG GCG ATG GCG GCG ACC   126
Val Met Thr Leu Ala Thr Thr His Ala Ala Met Ala Ala Thr
    -15             -10                     -5

GCG CCC GCC GAT GGC TAC GCG GCG ACG CGT TAT CCG ATC ATC   168
 Ala Pro Ala Asp Gly Tyr Ala Ala Thr Arg Tyr Pro Ile Ile
         1           5                     10

CTC GTG CAC GGG CTC TCG GGT ACC GAC AAG TAC GCC GGC GTG   210
Leu Val His Gly Leu Ser Gly Thr Asp Lys Tyr Ala Gly Val
        15                  20                  25

GTC GAG TAT TGG TAT GGC ATC CAG GAA GAC CTG CAG CAG AAC   252
Val Glu Tyr Trp Tyr Gly Ile Gln Glu Asp Leu Gln Gln Asn
            30                  35                  40

GGT GCG ACC GTC TAC GTC GCG AAC CTG TCG GGG TTC CAG AGC   294
Gly Ala Thr Val Tyr Val Ala Asn Leu Ser Gly Phe Gln Ser
                45                  50

GAC GAC GGC GCG AAC GGG CGC GGC GAA CAG TTG CTC GCT TAC   336
Asp Asp Gly Ala Asn Gly Arg Gly Glu Gln Leu Leu Ala Tyr
55              60                  65

GTG AAG ACG GTG CTC GCG GCG ACG GGC GCG ACC AAG GTC AAT   378
Val Lys Thr Val Leu Ala Ala Thr Gly Ala Thr Lys Val Asn
    70                  75                  80

CTC GTC GGC CAC AGC CAG GGC GGC CTC ACG TCG CGC TAT GTC   420
Leu Val Gly His Ser Gln Gly Gly Leu Thr Ser Arg Tyr Val
            85                  90                  95

GCG GCC GTC GCG CCC GAT CTC GTG GCG TCG GTG ACG ACG ATC   462
Ala Ala Val Ala Pro Asp Leu Val Ala Ser Val Thr Thr Ile
                100                 105                 110

GGC ACG CCG CAT CGC GGC TCC GAG TTT GCC GAC TTC GTG CAG   504
Gly Thr Pro His Arg Gly Ser Glu Phe Ala Asp Phe Val Gln
                    115                 120

AAC GTG CTG GCG TAC GAT CCG ACC GGG CTT TCG TCA TCG GTG   546
```

```
Asn Val Leu Ala Tyr Asp Pro Thr Gly Leu Ser Ser Val
125             130             135

ATC GCC GCG TTC GTC AAT GTG TTC GGC ATC CTG ACG AGC AGC   588
Ile Ala Ala Phe Val Asn Val Phe Gly Ile Leu Thr Ser Ser
    140             145             150

AGC CAC AAC ACG AAC CAG GAC GCG CTC GCC GCG CTG CAG ACG   630
Ser His Asn Thr Asn Gln Asp Ala Leu Ala Ala Leu Gln Thr
        155             160             165

CTG ACC ACC GCC CGG GCT GCC ACG TAC AAC CAG AAC TAT CCG   672
Leu Thr Thr Ala Arg Ala Ala Thr Tyr Asn Gln Asn Tyr Pro
            170             175             180

AGC GCG GGC CTG GGT GCG CCG GGC AGT TGC CAG ACC GGC GCG   714
Ser Ala Gly Leu Gly Ala Pro Gly Ser Cys Gln Thr Gly Ala
                185             190

CCG ACC GAA ACC GTC GGC GGC AAC ACG CAC CTG CTG TAT TCG   756
Pro Thr Glu Thr Val Gly Gly Asn Thr His Leu Leu Tyr Ser
195             200             205

TGG GCC GGC ACG GCG ATC CAG CCG ACG CTT TCG GTG TTC GGC   798
Trp Ala Gly Thr Ala Ile Gln Pro Thr Leu Ser Val Phe Gly
    210             215             220

ATC ACG GGC GCG ACC GAC ACG AGC ACC GTT CCG CTC GTT GAT   840
Ile Thr Gly Ala Thr Asp Thr Ser Thr Val Pro Leu Val Asp
        225             230             235

CTG GCG AAC GTG CTC GAC CCG TCG ACG CTC GCG CTG TTC GGC   882
Leu Ala Asn Val Leu Asp Pro Ser Thr Leu Ala Leu Phe Gly
            240             245             250

ACC GGC ACG GTG ATG ATC AAC CGC GGC TCC GGG CAG AAC GAC   924
Thr Gly Thr Val Met Ile Asn Arg Gly Ser Gly Gln Asn Asp
                255             260

GGG CTC GTG TCG AAG TGC AGT GCG CTG TAC GGC AAG GTG CTG   966
Gly Leu Val Ser Lys Cys Ser Ala Leu Tyr Gly Lys Val Leu
265             270             275

AGT ACG AGC TAC AAG TGG AAC CAC CTC GAC GAG ATC AAC       1005
Ser Thr Ser Tyr Lys Trp Asn His Leu Asp Glu Ile Asn
    280             285             290

CAG CTG CTC GGC GTG CGC GGC GCG TAT GCG GAA GAT CCG       1044
Gln Leu Leu Gly Val Arg Gly Ala Tyr Ala Glu Asp Pro
        295             300

GTC GCG GTG ATC CGC ACG CAT GCG AAC CGG CTG AAG CTG       1083
Val Ala Val Ile Arg Thr His Ala Asn Arg Leu Lys Leu
305             310             315

GCG GGC GTG TAA                                            1095
Ala Gly Val
        320
```